United States Patent [19]

James, Jr.

[11] Patent Number: 5,316,663
[45] Date of Patent: * May 31, 1994

[54] PROCESS FOR THE TREATMENT OF HALOGENATED HYDROCARBONS

[75] Inventor: Robert B. James, Jr., Northbrook, Ill.

[73] Assignee: UOP, Des Plaines, Ill.

[*] Notice: The portion of the term of this patent subsequent to May 24, 2011 has been disclaimed.

[21] Appl. No.: 819,737

[22] Filed: Jan. 13, 1992

[51] Int. Cl.$^5$ .............................................. C01G 45/04
[52] U.S. Cl. .............................. 208/262.1; 208/262.5
[58] Field of Search ........................... 208/262.1, 262.5

[56] References Cited

U.S. PATENT DOCUMENTS

| | | | |
|---|---|---|---|
| 4,810,365 | 3/1989 | Dohler | 208/262 |
| 4,818,368 | 4/1989 | Kalnes | 208/57 |
| 4,849,095 | 7/1989 | Johnson | 208/262 |
| 4,923,590 | 5/1990 | Kalnes | 208/85 |
| 4,952,746 | 8/1990 | Johnson | 208/262.1 |
| 4,956,076 | 9/1990 | Awbry | 208/262.8 |
| 5,013,424 | 5/1991 | James, Jr. | 208/262.5 |
| 5,043,054 | 8/1991 | Halpern | 208/262.5 |

*Primary Examiner*—Helane Myers
*Attorney, Agent, or Firm*—Thomas K. McBride; John G. Tolomei; John C. Cutts, Jr.

[57] ABSTRACT

A process to convert organic waste streams containing halide compounds to produce hydrogenated organic compounds and to recover the resulting hydrogen halide as an anhydrous product stream.

8 Claims, 1 Drawing Sheet

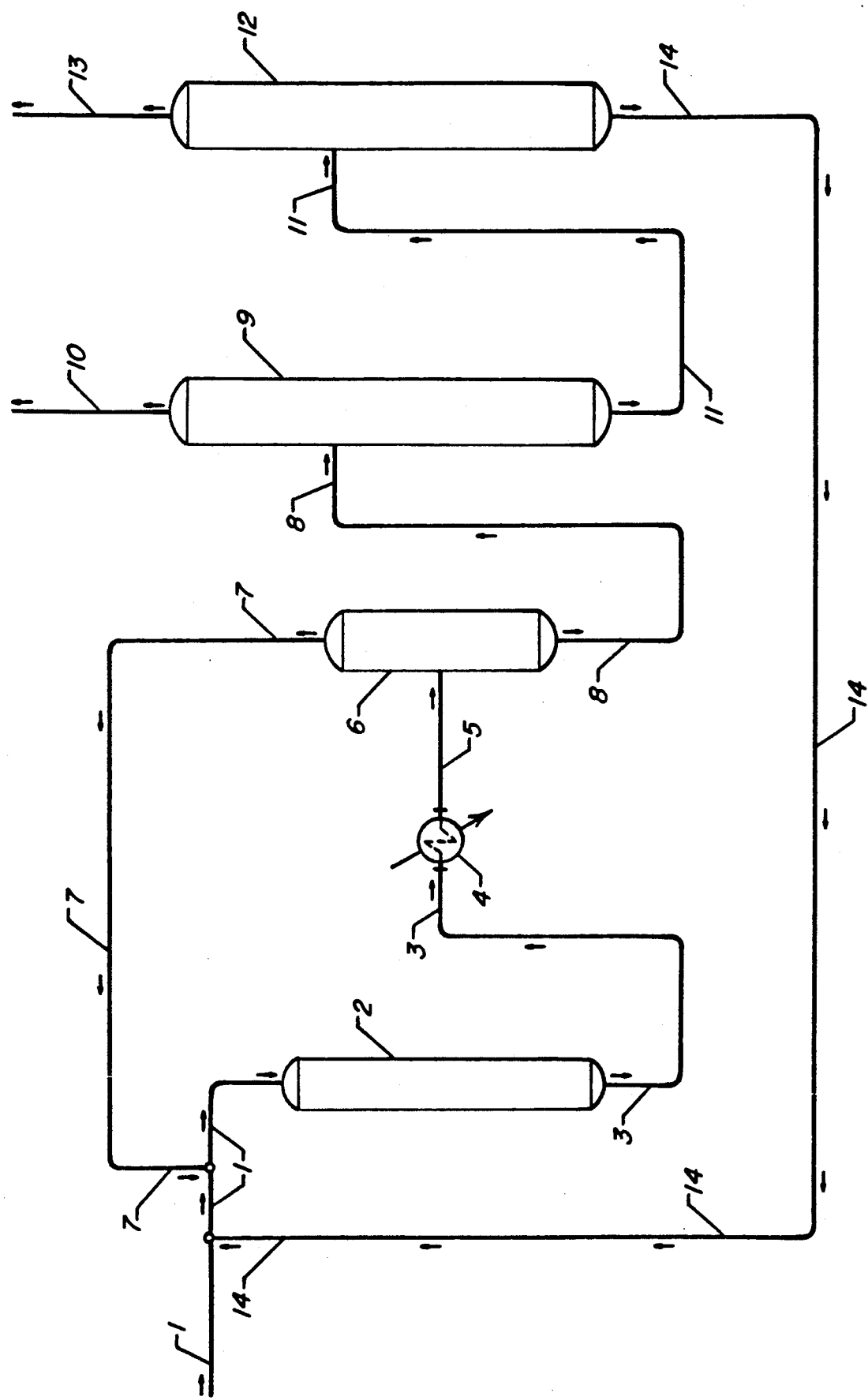

PROCESS FOR THE TREATMENT OF HALOGENATED HYDROCARBONS

BACKGROUND OF THE INVENTION

The field of art to which this invention pertains is the production of a hydrogenated hydrocarbonaceous product and an anhydrous hydrogen halide stream from a halogenated organic stream.

There is a steadily increasing demand for technology which is capable of treating an organic stream containing halogenated compounds to produce hydrogenated organic compounds and a hydrogen halide stream. The preferred hydrogen halide stream is anhydrous which minimizes the cost of building the processing plant based upon metallurgical considerations.

With the increased environmental emphasis for the treatment and recycle of organic waste streams containing halogenated compounds, there is an increased need for improved processes to convert the organic waste stream to produce hydrogenated organic compounds and hydrogen halide. For example, during the disposal or recycle of potentially environmentally harmful organic waste streams, an important step in the total solution to the problem is to produce an organic stream which facilitates the ultimate resolution to produce product streams which may subsequently be handled in an environmentally acceptable manner. One environmentally attractive method of treating organic waste streams is by hydrogenation. Therefore, those skilled in the art have sought to find feasible and economical techniques to convert organic waste streams containing halide compounds to hydrogenated organic compounds and to recover the concomitantly produced hydrogen halide. When the hydrogen halide is recovered by means of some type of aqueous scheme or system, the metallurgy requirements become an economic consideration and, therefore, it has recently become highly desirable where possible to recover the resulting hydrogen halide via an anhydrous method.

INFORMATION DISCLOSURE

In U.S. Pat. No. 4,923,590 (Kalnes et al), a process is disclosed wherein the effluent from a hydrogenation reaction zone is contacted with an aqueous scrubbing solution. In one embodiment, the '590 patent teaches that when the feed to the hydrogenation zone comprises halogenated compounds, the aqueous scrubbing solution preferably contains a basic compound to neutralize the acid.

BRIEF SUMMARY OF THE INVENTION

The invention provides an improved process to convert organic waste streams containing halide compounds to hydrogenated organic compounds and to recover the resulting hydrogen halide as an anhydrous product stream.

One embodiment of the invention may be characterized as a process for treating a halogenated organic stream to produce a hydrogenated hydrocarbonaceous stream having a reduced level of halogen and an anhydrous stream comprising a hydrogen halide which process comprises the steps of: (a) contacting the halogenated organic stream, a hydrogen-rich gaseous recycle stream and a recycle stream comprising unreacted halogenated organic compounds with a hydrogenation catalyst in a hydrogenation reaction zone at hydrogenation conditions to increase the hydrogen content of the halogenated organic stream and to thereby produce hydrogen halide; (b) condensing at least a portion of the resulting effluent from the hydrogenation reaction zone to produce the hydrogen-rich gaseous recycle stream and a liquid stream comprising hydrogenated hydrocarbonaceous compounds and hydrogen halide; (c) separating the liquid stream comprising hydrogenated hydrocarbonaceous compounds and hydrogen halide to produce an anhydrous stream comprising hydrogen halide and a stream comprising hydrogenated hydrocarbonaceous compounds and unreacted halogenated organic compounds; and (d) separating the stream comprising hydrogenated hydrocarbonaceous compounds and unreacted halogenated organic compounds to produce the recycle stream comprising unreacted halogenated organic compounds and the hydrogenated hydrocarbonaceous stream having a reduced level of halogen.

Other embodiments of the present invention encompass further details such as preferred feedstocks, hydrogenation catalysts and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved integrated process for the conversion of a halogenated hydrocarbonaceous stream to produce a hydrogenated hydrocarbonaceous stream having a reduced level of halogen and an anhydrous stream comprising a hydrogen halide. There is a steadily increasing demand for technology which is capable of treating halogenated hydrocarbonaceous compounds and, in particular, for a process which is capable of recovering an anhydrous stream of hydrogen halide which thereby provides an economical treating process which eliminates or at least minimizes the use of expensive construction materials for the processing plant.

A wide variety of halogenated organic compounds, both unsaturated and saturated, are candidates for feed streams in accordance with the process of the present invention. Examples of organic streams comprising halogenated organic compounds which are suitable for treatment by the process of the present invention are dielectric fluids, hydraulic fluids, heat transfer fluids, used lubricating oil, used cutting oils, used solvents, halogenated hydrocarbonaceous by-products, oils contaminated with polychlorinated biphenyls (PCB), halogenated wastes, petrochemical by-products and other halogenated hydrocarbonaceous industrial wastes. Often, in a particular place or location, two or more halogenated organic streams are present and require further treatment. The halogenated organic compounds may also contain hydrogen and are therefore then referred to as hydrocarbonaceous compounds.

In accordance with the present invention, the halogenated organic feedstock preferably contains less than about 500 ppm by weight of water or water precursors. Examples of water precursors are oxygenated compounds which, when subjected to hydrogenation conditions, are converted into hydrogenated compounds and water. As used herein, the term "anhydrous stream comprising hydrogen halide" connotes a stream having less than about 50 ppm by weight of water.

Preferred feedstocks comprise a component selected from the group consisting of fractionation column bottoms in the production of allyl chloride, fractionation column bottoms in the production of ethylene dichloride, fractionation column bottoms in the production of trichloroethylene and perchlorethylene, used dielectric fluid containing polychlorinated biphenyls (PCB) and halogenated benzene, used solvents, fractionation bottoms from the purification column in epichlorohydrin production, carbon tetrachloride, 1,1,1-trichloroethane, halogenated alcohols, halogenated ethers, chlorofluorocarbons and admixtures thereof.

The halogenated organic compounds which are contemplated as feedstocks in the present invention may contain a halogen selected from the group consisting of chlorine, bromine, fluorine and iodine. Preferred halogen compounds contain a halogen selected from the group consisting of chlorine and fluorine.

In accordance with the present invention, a feedstock containing halogenated organic compounds is introduced in admixture with a hydrogen-rich, gaseous recycle stream and a recycle stream comprising unreacted halogenated hydrocarbonaceous compounds into a catalytic hydrogenation zone containing hydrogenation catalyst and maintained at hydrogenation conditions. This catalytic hydrogenation zone may contain a fixed, ebullated or fluidized catalyst bed. This reaction zone is preferably maintained at conditions which are chosen to dehalogenate the halogenated organic compounds which are introduced thereto. The catalytic hydrogenation zone is preferably maintained under an imposed pressure from about atmospheric to about 2000 psig and more preferably under a pressure from about 100 psig to about 1800 psig. Suitably, such reaction is conducted with a maximum catalyst bed temperature in the range of about 122° F. (50° C.) to about 850° F. (454° C.) selected to perform the desired dehalogenation conversion to reduce or eliminate the concentration of halogenated organic compounds contained in the combined feed stream. In accordance with the present invention, it is contemplated that the desired hydrogenation conversion includes, for example, dehalogenation and hydrocracking. Further preferred operating conditions include liquid hourly space velocities in the range from about 0.05 hr$^{-1}$ to about 20 hr$^{-1}$ and hydrogen circulation rates from about 200 standard cubic feet per barrel (SCFB) to about 100,000 SCFB, preferably from about 200 SCFB to about 50,000 SCFB.

In accordance with the present invention, the hydrocarbonaceous effluent containing at least one hydrogen halide compound from the hydrogenation zone is cooled and introduced into a vapor-liquid separator to produce a hydrogen-rich, gaseous recycle stream and a liquid stream comprising hydrogenated hydrocarbonaceous compounds and hydrogen halide. The resulting liquid stream comprising hydrogenated hydrocarbonaceous compounds and hydrogen halide is separated to produce an anhydrous stream comprising hydrogen halide and a liquid stream comprising hydrogenated hydrocarbonaceous compounds and unreacted organic compounds. This resulting liquid stream is then separated to produce a recycle stream comprising unreacted halogenated organic compounds which is introduced into the hydrogenation reaction zone and a hydrogenated hydrocarbonaceous stream having a reduced level of halogen. In accordance with the present invention, the hydrogen halide compound is recovered as an anhydrous product stream. This permits the subsequent recovery and use of a desirable and valuable hydrogen halide compound.

The preferred catalytic composite disposed within the hereinabove described hydrogenation zone can be characterized as containing a metallic component having hydrogenation activity, which component is combined with a suitable refractory carrier material of either synthetic or natural origin. The precise composition and method of manufacturing the carrier material is not considered essential to the present invention. Preferred carrier materials are alumina, silica, carbon and mixtures thereof. Suitable metallic components having hydrogenation activity are those selected from the group comprising the metals of Groups VIB and VIII of the Periodic Table, as set forth in the *Periodic Table of Elements,* E. H. Sargent and Company, 1964. Thus, the catalytic composite may comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VIB are generally present in an amount within the range of from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. It is further contemplated that hydrogenation catalytic composites may comprise one or more the following components: cesium, francium, lithium, potassium, rubidium, sodium, copper, gold, solver, cadmium, mercury and zinc. Preferred hydrogenation catalysts comprise alumina and palladium.

As described above, the resulting hydrogenated hydrocarbonaceous effluent from the hydrogenation reaction zone is preferably separated to produce a hydrogen-rich gas phase and a liquid hydrocarbonaceous stream in a separation zone which is maintained at essentially the same pressure as the hydrogenation reaction zone and at a temperature in the range from about −70° F. (−57° C.) to about 40° F. (4.4° C.), and as a consequence, the liquid hydrocarbonaceous stream contains dissolved hydrogen, dissolved hydrogen halide and low molecular weight normally gaseous hydrocarbons if present. In accordance with the present invention, the hydrogenated liquid phase comprising the hydrogen chloride is separated to produce an anhydrous hydrogen halide stream by separating, for example, by stripping, flashing or fractionating. After the hydrogen halide stream has been produced and removed from the process, a resulting hydrocarbonaceous stream is separated to produce a hydrocarbonaceous stream, primarily comprising hydrogenated hydrocarbonaceous compounds and a stream primarily comprising halogenated organic compounds which may then be recycled to the hydrogenation conversion zone if desired. Such a separation may be conducted in any convenient manner such as, for example, stripping, flashing or fractionating.

In the drawing, the process of the present invention is illustrated by means of a simplified flow diagram in which such details as total number of reaction zone and drier vessels, pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

DETAILED DESCRIPTION OF THE DRAWING

With reference now to the drawing, a halogenated organic feed stream containing halogenated organic compounds is introduced into the process via conduit 1 and is contacted with a hydrogen-rich gaseous recycle stream which is provided via conduit 7 and is hereinafter described. The halogenated organic feed stream containing halogenated organic compounds, the hydrogen-rich gaseous recycle stream and an unconverted halogenated organic recycle stream provided via conduit 14 and hereinafter described are introduced into hydrogenation reaction zone 2. The resulting hydrogenated organic stream is removed from the hydrogenation reaction zone 2 via conduit 3, is cooled in heat exchanger 4 and introduced into vapor liquid separator 6 via conduit 5. A hydrogen-rich gaseous stream is removed from vapor-liquid separator 6 via conduit 7 and recycled as described hereinabove. Since hydrogen is lost in the process by means of a portion of the hydrogen being dissolved in the exiting liquid hydrocarbon and hydrogen being consumed during the hydrogenation reaction, it is necessary to supplement the hydrogen-rich gaseous stream with a make-up hydrogen from some suitable external source, for example, a catalytic reforming unit or a hydrogen plant. Make-up hydrogen may be introduced into the system at any convenient and suitable point which is not shown on the drawing. A liquid hydrogenated hydrocarbonaceous stream containing hydrogen and a hydrogen halide in solution is removed from vapor liquid separator 6 and is introduced into fractionation zone 9 via conduit 8. A product stream containing hydrogen halide is removed from fractionation zone 9 via conduit 10 and recovered. A liquid distillable hydrogenated hydrocarbonaceous stream is removed from fractionation zone 9 via conduit 11 and is introduced into fractionation zone 12. A product stream containing hydrocarbonaceous compounds having a reduced concentration of halogen is removed from fractionation zone 12 via conduit 13 and recovered. A liquid stream containing unconverted halogenated organic compounds is removed from fractionation zone 12 via conduit 14 and is recycled to hydrogenation reaction zone 2 via conduit 14 as described hereinabove.

The following example is presented for the purpose of further illustrating the process of the present invention and to indicate the benefits afforded by the utilization thereof in producing a hydrogenated hydrocarbonaceous stream and an anhydrous stream comprising a hydrogen halide from a halogenated organic stream.

EXAMPLE

A halogenated organic feedstock having the characteristics presented in Table 1 is charged at a rate of 47.8 mol/hr to a hydrogenation reaction zone containing a palladium on alumina catalyst which is conducted at hydrogenation conditions which included a temperature of 176° F. (80° C.), a pressure of 750 psig (5171 kPa gauge) and a hydrogen circulation rate of 20,000 SCFB (3370 normal m$^3$/m$^3$).

TABLE 1

| HALOGENATED ORGANIC FEEDSTOCK PROPERTIES | |
|---|---|
| Composition, Weight Percent | |
| Chlorinated Propane | 91.1 |
| Unsaturated Propane | 4.7 |
| Other | 4.2 |

A recycle stream containing unconverted feedstock and hereinafter described is also charged to the hydrogenation reaction zone in an amount of 30 mol/hr.

The resulting effluent from the hydrogenation reaction zone is cooled to a temperature of about −15° C. and introduced into a vapor-liquid separator. A hydrogen-rich gaseous stream is removed from the vapor-liquid separator and which stream contains about 2000 mol/hr of hydrogen, 850 mol/hr of hydrogen chloride and about 70 mol/hr of chlorinated hydrocarbons. A liquid stream is removed from the vapor-liquid separator in an amount of about 140 mol/hr including about 50 mol/hr of propane, about 60 mol/hr of hydrogen chloride and about 25 mol/hr of chlorinated hydrocarbons. This resulting liquid stream is fractionated to produce a hydrogen chloride product stream containing about 60 mol/hr of hydrogen chloride, a propane product stream containing about 48 mol/hr propane and a liquid recycle stream containing about 30 mol/hr of chlorinated hydrocarbons.

The foregoing description, drawing and example clearly illustrate the advantages encompassed by the process of the present invention and the benefits to be afforded with the use thereof.

What is claimed:

1. A process for treating a halogenated organic stream to produce a hydrogenated hydrocarbonaceous stream having a reduced level of halogen and an anhydrous stream comprising a hydrogen halide which process comprises the steps of:

(a) contacting said halogenated organic stream, a hydrogen-rich, gaseous recycle stream and a recycle stream comprising unreacted halogenated organic compounds with a hydrogenation catalyst in a hydrogenation reaction zone at hydrogenation conditions to increase the hydrogen content of said halogenated organic stream and to thereby produce hydrogen halide;

(b) condensing at least a portion of the resulting effluent from said hydrogenation reaction zone to produce said hydrogen-rich gaseous recycle stream and a liquid stream comprising hydrogenated hydrocarbonaceous compounds and hydrogen halide;

(c) separating said liquid stream comprising hydrogenated hydrocarbonaceous compounds and hydrogen halide to produce an anhydrous stream comprising hydrogen halide and a stream comprising hydrogenated hydrocarbonaceous compounds and unreacted halogenated organic compounds; and (d) separating said stream comprising hydrogenated hydrocarbonaceous compounds and unreacted halogenated organic compounds to produce said recycle stream comprising unreacted halogenated organic compounds and said hydrogenated hydrocarbonaceous stream having a reduced level of halogen.

2. The process of claim 1 wherein said halogenated organic stream comprises a component selected from the group consisting of fractionation column bottoms in the production of allyl chloride, fractionation column bottoms in the production of ethylene dichloride, fractionation column bottoms in the production of trichloroethylene and perchlorethylene, used dielectric fluid containing polychlorinated biphenyls (PCB) and halogenated benzene, used solvents, fractionation bottoms from the purification column in epichlorohydrin production, carbon tetrachloride, 1,1,1-trichloroethane, halogenated alcohols, halogenated ethers, chlorofluorocarbons and admixtures thereof.

3. The process of claim 1 wherein said halogenated organic stream contains less than about 500 ppm by weight of water or water precursors.

4. The process of claim 1 wherein said anhydrous stream comprising hydrogen halide contains less than about 50 ppm by weight of water.

5. The process of claim 1 wherein said hydrogenation reaction zone is operated at conditions which include a pressure from about atmospheric to about 2000 psig, a maximum catalyst temperature from about 122° F. (50° C.) to about 850° F. (454° C.) and a hydrogen circulation rate from about 200 SCFB (33.7 normal m$^3$/m$^3$) to about 50,000 SCFB (8427 normal m$^3$/m$^3$).

6. The process of claim 1 wherein said hydrogenation catalyst comprises a refractory inorganic oxide and at least one metallic compound having hydrogenation activity.

7. The process of claim 6 wherein said metallic compound is selected from the metals of Groups VIB and VIII of the Periodic Table.

8. The process of claim 1 wherein said hydrogen halide is selected from the group consisting of hydrogen chloride, hydrogen bromide, hydrogen fluoride and hydrogen iodide.

* * * * *